(12) United States Patent
Mestrovic et al.

(10) Patent No.: US 9,427,179 B2
(45) Date of Patent: *Aug. 30, 2016

(54) SYSTEM, GARMENT AND METHOD

(71) Applicant: SENSORIA INC., Redmond, WA (US)

(72) Inventors: Michael Anthony Mestrovic, Moriac (AU); Pamela Margaret Petersen, Highton (AU); Robin William Cranston, Ivanhoe (AU); Warren Bradley Stannard, Wallington (AU); Patrick Brendan D'Arcy, Grovedale (AU)

(73) Assignee: Sensoria Inc., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/941,392

(22) Filed: Nov. 13, 2015

(65) Prior Publication Data

US 2016/0066821 A1 Mar. 10, 2016

Related U.S. Application Data

(62) Division of application No. 12/674,405, filed as application No. PCT/AU2008/001245 on Aug. 22, 2008, now Pat. No. 9,186,092.

(30) Foreign Application Priority Data

Aug. 22, 2007 (AU) ................................ 2007904520

(51) Int. Cl.
*A61B 5/00* (2006.01)
*A61B 5/11* (2006.01)
(Continued)

(52) U.S. Cl.
CPC .................. *A61B 5/112* (2013.01); *A61B 5/01* (2013.01); *A61B 5/1038* (2013.01); *A61B 5/1121* (2013.01); *A61B 5/14517* (2013.01); *A61B 5/6807* (2013.01); *A61B 5/4261* (2013.01)

(58) Field of Classification Search
CPC ...... A61B 5/11; A61B 5/112; A61B 5/1036; A61B 5/1038; A61B 5/6807; A61B 5/6829
See application file for complete search history.

(56) References Cited

U.S. PATENT DOCUMENTS

| 4,813,436 A | 3/1989 | Au ................................ 600/592 |
| 4,862,743 A | 9/1989 | Seitz ............................... 73/172 |

(Continued)

FOREIGN PATENT DOCUMENTS

| DE | 103 14 211 A1 | 11/2003 |
| EP | 1 938 749 A2 | 7/2008 |

(Continued)

OTHER PUBLICATIONS

International Search Report for PCT Application No, PCT/AU2008/001245, 3 pages, Nov. 4, 2008.

(Continued)

*Primary Examiner* — Max Hindenburg
(74) *Attorney, Agent, or Firm* — DWC Law Firm, P.S.; David Chen

(57) ABSTRACT

The present invention relates to a system and garment that incorporates sensors that can be used for measuring or monitoring pressure or forces in feet, the stumps of limbs of an amputee that are fitted with prosthetic devices, or any other parts of the body that are subject to forces such as the buttock while seated or when external pressure inducing devices are employed, such as for example, pressure bandages. The invention also relates to a method to monitor or diagnose any foot or limb related activity for recreational, sporting, military or medical reasons and is particularly aimed at the treatment of neuropathic or other degenerating conditions.

30 Claims, 9 Drawing Sheets

(51) Int. Cl.
*A61B 5/01* (2006.01)
*A61B 5/103* (2006.01)
*A61B 5/145* (2006.01)

(56) References Cited

U.S. PATENT DOCUMENTS

| | | | |
|---|---|---|---|
| 5,253,654 A | 10/1993 | Thomas et al. | 600/592 |
| 5,323,650 A | 6/1994 | Fullen et al. | 73/172 |
| 5,357,696 A | 10/1994 | Gray et al. | 36/135 |
| 5,546,955 A | 8/1996 | Wilk | 600/549 |
| 5,642,096 A | 6/1997 | Leyerer et al. | 340/573.1 |
| 6,145,551 A | 11/2000 | Jayaraman et al. | |
| 6,155,120 A | 12/2000 | Taylor | |
| 6,174,294 B1 | 1/2001 | Crabb et al. | |
| 6,216,545 B1 | 4/2001 | Taylor | |
| 6,315,009 B1 | 11/2001 | Jayaraman et al. | |
| 6,360,597 B1 | 3/2002 | Hubbard, Jr. | 73/172 |
| 6,381,482 B1 | 4/2002 | Jayaraman et al. | |
| 6,474,367 B1 | 11/2002 | Jayaraman et al. | |
| 6,500,210 B1 | 12/2002 | Sabolich et al. | 623/24 |
| 6,611,962 B2 | 9/2003 | Redwood et al. | |
| 6,687,523 B1 | 2/2004 | Jayaramen et al. | |
| 6,796,949 B2 | 9/2004 | Horton | |
| 6,836,744 B1 | 12/2004 | Asphahani et al. | 702/141 |
| 6,918,883 B2 | 7/2005 | Horton et al. | |
| 6,941,775 B2 | 9/2005 | Sharma | |
| 6,970,731 B1 | 11/2005 | Jayaraman et al. | |
| 7,319,895 B2 | 1/2008 | Klefstad-Sillonville et al. | |
| 7,395,614 B1 | 7/2008 | Bailey, Sr. et al. | |
| 7,426,873 B1 | 9/2008 | Kholwadwala et al. | 73/818 |
| 7,484,408 B2 | 2/2009 | Healey | |
| 7,522,951 B2 | 4/2009 | Gough et al. | 600/388 |
| 7,559,902 B2 | 7/2009 | Ting et al. | |
| 7,587,937 B2 * | 9/2009 | Haselhurst et al. | 73/172 |
| 7,601,126 B2 | 10/2009 | Keegan et al. | 600/595 |
| 7,726,206 B2 | 6/2010 | Terrafranca, Jr. et al. | |
| 7,758,523 B2 | 7/2010 | Collings et al. | 600/592 |
| 7,770,473 B2 | 8/2010 | Von Lilienfeld-Toal et al. | |
| 7,878,055 B2 | 2/2011 | Balzano | 73/172 |
| 7,997,007 B2 | 8/2011 | Sanabria-Hernandez | |
| 7,998,092 B2 | 8/2011 | Avni et al. | 600/587 |
| 8,081,083 B2 | 12/2011 | Hinterlong | |
| 8,099,258 B2 | 1/2012 | Alten et al. | |
| 8,109,890 B2 | 2/2012 | Kamiar et al. | |
| 8,116,898 B2 | 2/2012 | Chung et al. | |
| 8,140,143 B2 | 3/2012 | Picard et al. | |
| 8,167,824 B2 | 5/2012 | Iwata et al. | 600/592 |
| 8,348,841 B2 | 1/2013 | Varadan | |
| 8,352,211 B2 | 1/2013 | Vock et al. | |
| 8,389,862 B2 | 3/2013 | Arora et al. | |
| 8,416,088 B2 | 4/2013 | Ortega et al. | |
| 8,443,634 B2 | 5/2013 | Scheffler et al. | |
| 8,583,272 B2 | 11/2013 | Spector | |
| 8,661,915 B2 | 3/2014 | Taylor | |
| 8,676,541 B2 | 3/2014 | Schrock et al. | |
| 8,925,392 B2 * | 1/2015 | Esposito et al. | 73/862.01 |
| 9,028,430 B2 * | 5/2015 | Woo et al. | 600/595 |
| 2003/0224155 A1 | 12/2003 | Orth et al. | |
| 2007/0245504 A1 | 10/2007 | Spector | |
| 2008/0001735 A1 | 1/2008 | Tran | |
| 2008/0160851 A1 | 7/2008 | Dunn et al. | |
| 2008/0161731 A1 | 7/2008 | Woods | |
| 2008/0171914 A1 | 7/2008 | Ouwerkerk et al. | |
| 2008/0287832 A1 | 11/2008 | Collins et al. | |
| 2008/0307899 A1 | 12/2008 | Von Lilienfeld-Toal et al. | |
| 2009/0205879 A1 | 8/2009 | Halsey, IV et al. | |
| 2011/0004072 A1 | 1/2011 | Fletcher et al. | |
| 2011/0015498 A1 | 1/2011 | Mestrovic et al. | |
| 2011/0054359 A1 | 3/2011 | Sazonov et al. | |
| 2011/0119812 A1 | 5/2011 | Genz et al. | |
| 2011/0263950 A1 | 10/2011 | Larson et al. | |
| 2011/0267196 A1 | 11/2011 | Hu et al. | |
| 2012/0035509 A1 | 2/2012 | Wilson et al. | |
| 2012/0086550 A1 | 4/2012 | LeBlanc et al. | |
| 2012/0109013 A1 | 5/2012 | Everett et al. | |
| 2012/0184878 A1 | 7/2012 | Najafi et al. | |
| 2013/0137943 A1 | 5/2013 | Pinto Rodrigues | |
| 2013/0185003 A1 | 7/2013 | Carbeck et al. | |
| 2013/0211208 A1 | 8/2013 | Varadan et al. | |
| 2013/0245414 A1 | 9/2013 | Andrioni et al. | |
| 2013/0281795 A1 | 10/2013 | Varadan | |
| 2013/0281815 A1 | 10/2013 | Varadan | |

FOREIGN PATENT DOCUMENTS

| | | |
|---|---|---|
| GB | 2 439 750 A | 1/2008 |
| GB | 2 443 208 A | 4/2008 |
| GB | 2 445 760 A | 7/2008 |
| GB | 2 439 750 A | 1/2009 |
| JP | 2004-132765 | 4/2004 |
| WO | WO 01/43638 | 6/2001 |
| WO | 2006/030405 A1 | 3/2006 |
| WO | WO 2006/030405 | 3/2006 |
| WO | WO 2007/059971 | 5/2007 |

OTHER PUBLICATIONS

Andreoni, Giuseppe et al., "A Review of the Intellectual Property Rights in the Field of Wearable Sensors and Systems," International Journal of Computer Research, vol. 18, No. 3/4, pp. 269-285 (2011).

Bucki, M. et al., "The TexiSense << Smart Sock >>~Textile Pressure Sensor and 3D Real-time Finite Element Model of the Diabetic Foot for a Daily Prevention of Pressure Ulcers," Proceedings of the 14th Annual European Pressure Ulcer Meeting, Oport. Portugal (2011).

NTT Press Releases, "Electrocardiography is achieved simply by wearing a piece of clothing that has textiie electrodes combined with conductive polymer," www.ntt.co.jp/news2013/1302e/130212a.html (2013).

Pacelli, M. et al., "Sensing Fabrics for Monitoring Physiological and Biomechanical Variables: E-textile solutions," Proceedings of the 3rd IEEE-EMBS, International Summer School and Symposium on Medical Devices and Biosensors, MIT, Boston, USA (Sep. 2006).

Rienzo, Diet al., "Textile technology for the vital signs monitoring in telemedicine and extreme environments," IEEE Trans. Inf. Technol. Biomed., vol. 14, No. 3, pp. 71 1-717; Abstract—www.ncbi.nim.nih gov/pubmed/20421189 (2010).

Tekscan, "Tekscan Adds A401 Sensor to Flexiforce Product Line," www.tekscan.com/a401-force-sensor-released (2007).

Torgan, Carol Ph.D, Self-Tracking Meets Ready-To-Wear: Make Room in Your Closet for Smart Clothes (Nov. 6, 2011).

Castano, Lina M. et al., "Smart Fabric sensors and e-textile technologies: a review," Smart Mater. Struct. 23, 27pp, (Apr. 2014).

Shyr, Tien-Wei et al., "A Textile-Based Wearable Sensing Device Designed for Monitoring the Flexion Angle of Elbow and Knee Movements,"Sensors, vol. 14, pp. 4050-4059 (2014).

Stoppa, Matteo et al., "Wearable Electronics and Smart Textiles: A Critical Review," Sensors, vol. 14, pp. 11957-11992 (2014).

* cited by examiner

SYSTEM, GARMENT AND METHOD

REFERENCE TO PRIORITY APPLICATIONS

This application is a divisional of U.S. patent application Ser. No. 12/674,405 filed Sep. 30, 2010, which is a '371 US Nat'l Phase of Int'l Patent Application No. PCT/AU2008/001245 filed Aug. 22, 2008, which claims priority to AU Patent Application No. 2007904520 filed Aug. 22, 2007. These patent applications are incorporated herein by reference in their entireties.

BACKGROUND

The present invention relates to a system and garment that incorporates sensors that can be used for measuring or monitoring pressure or forces in feet, the stumps of limbs of an amputee that are fitted with prosthetic devices, or any other parts of the body that are subject to forces such as the buttock while seated or when external pressure inducing devices are employed, for example, pressure bandages. The invention may also incorporate other sensors for monitoring physical conditions such as temperature, strain, stress or angulation or sensors for monitoring physiological conditions such as the makeup of sweat or body exudate. Moreover, the invention also relates to a method to monitor or diagnose any foot or limb related activity for recreational, sporting, military or medical reasons and is particularly aimed at the treatment of neuropathic or other degenerating conditions.

Diabetes, alcoholism, uremia, AIDs, or nutritional deficiencies are conditions that are well known as causing damage to nerve endings known as peripheral neuropathy. Other less common causes include exposure to cold or radiation, physical injuries, a few medicines, toxic substances, vascular or collagen disorders, systemic lupus erythematosus, scleroderma and rheumatoid arthritis. Symptoms of peripheral neuropathy are usually in the form of pain, numbness, tingling, burning or a loss of feeling. The symptoms may also include a sensation that you are wearing an invisible glove or sock; a burning or freezing pain; sharp, jabbing or electric pain; and an extreme sensitivity to touch.

Diabetes also affects the circulation. Poor circulation can affect the ability of the body to heal when damage occurs. Healing can take a while and it is imperative that pressure is removed from the area and good wound dressings are used, infections can spread, the ultimate of this process is an amputation. Neuropathy is the commonest complication of diabetes and usually arises within 5 years of the onset of the disease. Fifty percent of patients with neuropathic joints require some degree of amputation within 5 years.

Patients with peripheral neuropathy demonstrate a significant increase in loading time, mainly at the heel and at the metatarsal area of the foot, and they demonstrate a reduction at the hallux: i.e. they become flat footed and acquire a hip-based walking strategy. It has been established from discussions with leading world podiatrists and clinicians that a means for obtaining early diagnosis or identification of at risk patients would be of enormous advantage enabling early intervention to assist patients with long term solutions. What is required is a device that can provide a measured record of daily activity at the foot.

One attempt to address this problem is the Pedar system which is a pressure mapping system developed by Novel, Munich Germany. The system monitors local loading of the foot inside the shoe and is used for:

gait analysis
rehabilitation assessment
shoe research and design
aiding in shoe prescription and orthotic design
field testing of sport applications
kinetic analysis of free gait However, the system is not suitable for elderly or frail persons, or extended wearing by persons with venous illnesses such as diabetes. The other serious limitation is that these devices are shoe inserts and are therefore only effective when the person is wearing shoes. It is however desirable to gather information for all walking behavior with and without shoes.

Another attempt is described in German patent DE10314211 which relates to a sock that has a grid of conducting yarns that provide pressure measuring at points of intersection when a person is walking. The pressure-sensitive material extends over the entire foot region and provides an insight on the distribution of loads but does not measure pressure or loads in absolute terms nor does it measure other factors such as temperature and strain.

SUMMARY OF INVENTION

According to one embodiment of the present invention there is provided a system that is worn by a user to monitor or sense pressure either separately or in combination with any one or more of temperature, stress, strain, angulation or a physiological condition such as the make up of sweat or body exudate, the system including:

a) one or more than one discrete pressure sensor that can be fitted to, or worn against surfaces subjected to forces or pressure that include, but are by no means limited to, feet or stumps of a limb of an amputee; and b) electrical circuitry that receives signals from the sensors;

whereby, when in use, each sensor is able to be positioned at desired locations on the surfaces subject to forces or pressure of a user to monitor or sense pressure at the location of the sensors.

Throughout this specification, references to surfaces of a user subject to a forces include side surfaces such as the ankle or upper parts of the foot, and is not limited to parts of the body that are necessarily required to carry the load of the person such as the sole of a person's foot while walking or the buttock of the person while seated. In addition, the words "pressure" and "forces" are used synonymously throughout this specification. One of the advantages of the present invention is that the sensors may be strategically located to sense and monitor changes to a foot or limb condition throughout daily activity. In the instance when the invention is being used to monitor the pressure or forces on a person's foot, a clinician can position the sensors based on their understanding of the walking characteristics of the user to obtain the most relevant data from the sensors. In other words, the invention allows a level of customization to be achieved for individual users.

Preferably, the sensors are movable and can be selectively moved around different locations to monitor different parts of the user. Preferably, the system includes a substrate that can be worn by, or fitted directly or indirectly to the surfaces of the user being monitored, and said sensors are fixed or moveably connected to the substrate.

According to another embodiment of the present invention there is provided a system that is worn by a user to monitor or sense pressure either separately or in combination with any one or more of temperature, stress, strain, angulation or a physiological condition such as the make up of sweat or exudate of the user, the system including:

a) a flexible substrate that can be worn by, or fitted directly or indirectly to surfaces of a user subject to pressure or forces such as, but by no means limited to feet, or stumps of a limb of an amputee; and b) one or more than one discrete pressure sensor fixed or movably connected to the substrate, wherein the substrate and sensors can be worn directly or indirectly against surfaces of the user and the sensors can be positioned at desired locations without causing an increase in pressure in the load bearing surfaces as result of the presence of the pressure sensors.

One of the advantages of the present invention is that use of the sensors do not have any physical effect that could in any way cause adverse effects to the foot or limb at points of contact. Preferably, the system includes circuitry that receives signals from the sensors. According to another embodiment of the present invention there is provided a garment that is worn by a person to monitor or sense pressure either separately or in combination with any one or more of temperature, stress, strain, angulation or a physiological condition such as the make up of sweat or body exudate, the garment including:

a) a flexible substrate that can be worn by, or fitted directly or indirectly to surfaces of a user subject to loads or pressure such as, but by no means limited to feet, or stumps of a limb of an amputee; and b) one or more than one pressure sensor fixed or movably connected to the substrate, whereby, when the substrate is fitted or worn to the user, each pressure sensor is able to be positioned at desired locations on the surfaces of the user.

The position of the sensors is able to be adjusted by adjusting the position of the substrate on the user or, in the situation where the sensors are removeable, the position of individual sensors on the substrate may also be moved.

According to yet another embodiment of the present invention there is provided a garment that is worn by a person to monitor or sense pressure either separately or in combination with any one or more of temperature, stress, strain, angulation or a physiological condition such as the make up of sweat or body exudate, the garment including:

a) a flexible substrate that can be worn by, or fitted directly or indirectly to surfaces of a user subject to loads or pressure such as, but by no means limited to feet, or stumps of a limb of an amputee; and b) one or more than one pressure sensor fixed to removably connected to the substrate, wherein the substrate and pressure sensors can be worn directly or indirectly against surfaces of the user and the sensors can be positioned at desired locations without causing an increase in pressure in the surfaces of the sensors.

According to another embodiment of the present invention there is also provided a method of monitoring or treating a patient, the method including the steps of:

placing a pressure sensitive garment, sleeve or bandages in contact with the buttock, hand, foot or limb of a patient; and monitoring the pressure readings attributable to either the weight of the patient or the pressure applied externally to the patient, for example, the pressure gradient applied by pressure bandages to a limb of a patient.

The step of monitoring may involve analyzing the signals of pressure sensors located on any one or more part of the patients foot such as the ball, heel or toes of a patient including big toe, 1st, 3rd and $5^{th}$ metatarsal.

The method may also include the patient performing different movements such as walking, running, jumping, stopping and moving from a stationary position.

The method of the present invention may also include any one or a combination of the features of the pressure sensitive garment, sleeve, bandages or system as described herein.

DETAILED DESCRIPTION

A series of preferred features that may apply equally to both the system, garment and method embodiments of the invention will now be described. The ability of the sensor to not cause an increase in pressure at the surface of a user subject to loads or pressure may be achieved by a number of ways. For example, the substrate may contain recesses that house the sensors so as to provide a continuous smooth outer surface and the housing and sensors have substantially the same hardness or compression characteristics so as to maintain a relative smooth surface when the substrate is under load. However, rather than providing recesses in the substrate that accommodate the sensors, preferably the sensors have a low profile that is equal to or less than 5.0 mm in thickness, even more preferably equal to or less than 3.0 mm in thickness, and suitably less than or equal to 1.0 mm in thickness.

Even more preferably, the sensors have a thickness that is equal to or less than 0.5 mm, 0.05 mm, or suitably equal to or less than to 0.01 mm.

Preferably, the area of the sensors facing the user is equal to or less than 400 mm$^2$, and suitably equal to or less than 100 mm$^2$, or even more preferably less than 50 mm$^2$.

In the situation where the sensors are removably attached to the substrate, suitably, the sensors can be held in position on the substrate using either one or a combination of adhesive materials including releasable adhesives or sticky adhesives, hook and loop type fasteners, clasps or any other mechanical fasteners that has a lower profile or does not have an adverse effect on the user by creating an increase in pressure at a particular point.

According to an alternative embodiment, it is also possible for the sensors to be integrally incorporated in the structure of the substrate. For example, the sensors may be in the form of material located in discrete areas or selective areas that have been physically or chemically treated so as to be able to behave as a pressure sensor. Pressure sensitive material may be in the form of foam or fibrous material coated with conductive material, or pressure sensitive conductive fibers or yarns that are either added to a garment or form an integral part of the garment. For example, the substrate or a portion of the substrate may behave as a pressure sensor as a result of being treated with a conductive material in the form of a polymeric material such as polypyrrole or poly(ethylenedioxythiophene) PEDOT. The substrate may be any substrate including woven fabrics, non-woven fabrics, knitted fabrics such as single or double knitted jersey, terry knits and alike.

The substrate or the portion of the substrate treated with the conductive polymeric material may include electrodes in the form of two conductive threads, such as metal coated threads and suitably silver coated threads that measure changes in electrical potential difference between the threads. Suitably, the threads are spaced apart by a spacing in the range of 2 to 15 mm and ideally approximately 5 mm in a direction transverse to the direction in which the substrate compresses when a pressure is applied to the substrate.

Suitably the substrate when treated with conductive materials behaves as a pressure sensor whereby pressure applied to the substrate is proportional to the inverse of voltage change across the sensor.

In the situation where the sensors measure are used for monitoring the biomechanical movement of a user's foot, for example as may be useful for podiatry, neuropathy or orthotics investigations, analysis and treatment, preferably, the sensors are able to be located at the heel and metatarsal region of the foot. For example, the sensors may be located in a triangular formation at the heel of the user and located in alignment with the 1st, 3rd and 5th metatarsal of the foot.

One or more sensors may also be located in the arch of the user foot. Although it is possible that the sensors may be located between layers of the substrate, or embedded in the substrate, preferably, the sensors are located on an inner surface of the substrate that directly faces the surface of the user or an outer surface of the substrate that faces away from the user.

The substrate may be any form of garment depending on the particular application and body part being monitored such as socks, stockings, underpants, long johns, a singlet or a tubular sleeve. In the situation where feet of a diabetic or the stumps of an amputee are being monitored to prevent, for example, the formation of ulcers, preferably the substrate is in the form of a sock or stocking. The sock or stocking may be made from any suitable material and have any structure including knitted, woven or non-woven structures. It is also possible that the substrate may be in the form of an insert, bandage, sleeve, flexible planar materials, pads or inner garments that covers a foot or limb of a user. One of the advantages of this embodiment is that pressure sensors can be used to effectively measure the pressures applied by the bandages and thus provide a valuable means to determine the pressure gradient created by any pressure bandaging system. Applications involving monitoring and controlling pressure gradients produced through pressure bandages can be used for treating venous leg ulcers or lymphoedema. In addition, the pressure sensors can also provide a means to determine the performance of pressure bandaging on patients while the bandages are in use and the effect on the patient when moving from supine to standing positions.

According to another embodiment of the present invention, the garment may be in the form of a sleeve, suitably, a high stretch low pressure sleeve having pressure and temperature sensors. Once in place on a patient's limb, preferred pressure bandages can then be applied over the sleeve in a manner to produce the desired pressure gradient that is readily displayed as the bandages are applied.

In another example the garment can be used to monitor the pressure on a user's foot. The substrate, when used for this application and in other applications may be in the form of an insert that covers particular sections of a foot such as the metatarsal area of a foot, the heel of the foot, the arch of the foot, or the upper face of the foot. According to one particular embodiment, the substrate may be in the form of an inner sock that covers the foot up to the ankle and not the lower calf of the user and a conventional sock, covering the inner sock, ankle and calf of the user may be worn over the inner sock.

Preferably, the electrical circuitry is made up of at least two separable parts. Preferably the circuit includes a first part of the circuit that is disconnectable from the substrate such that it can be disconnected and reconnected from the substrate as desired. In the situation where the substrate is in the form of a sock, preferably the first part of the circuit includes valuable reusable components of the electrical circuit including: signal conditioning or manipulation for example to counteract noise from mains electricity, data storage, data processing units, data transmission units and optionally power sources such as batteries.

Depending on the particular application, the batteries may be rechargeable. Ideally, the components are contained in a housing that can be detachably connected to the substrate. Fastening means such as hook and loop type fasteners, couplings, clasps and press fasteners may be used to secure the housing in position to the substrate.

Preferably, the second part of the electrical circuit includes the sensors and leads that extend from the sensors to first part of the circuit.

Preferably, first part of the circuit and housing weighs less than 300 grams, suitably less than 200 grams and even more preferably less than 100 grams.

Preferably the first and second parts of the circuit contain co-operating pairs of contacts that electrically interconnect the first and second parts of the circuit. For example, the leads of the second part of the circuit terminate in pairs of contact surfaces, hereinafter referred to as the second contact surfaces and the housing containing the first part of the circuit also has a co-operating pair of contact surfaces, hereinafter referred to as the first contact surfaces. Suitably, the first contact surfaces face outwardly from the back or underside of the housing that is positioned against the substrate. In the situation where the substrate is in the form of a sock, 'preferably the second contact surfaces are located at the upper section or adjacent to the opening of the sock.

The leads may be in the form of conductive fibers, yarns or threads or ribbon and bus connections that are supported by the substrate. Although it is possible that the leads may be incorporated in the substrate preferably, the leads are sewn, knitted or woven to the substrate so that the substrate can flex and/or stretch in substantially the same manner as if the conductive yarns were absent. For instance leads in the form of ribbon and bus connections may flex and stretch in an elastic or resiliently deformable manner.

Alternatively, in the situation in which the leads such as ribbon and bus connectors are not elastic or resiliently deformable, it is possible that the leads may be supported on the substrate so as to move between a corrugated or tortuous condition, while the substrate is not flexed or stretched, to an at least partially or fully straightened condition, when the substrate is flexed or stretched.

Preferably, the system and garment of the present invention may also include any one or a combination of sensors for monitoring or sensing temperature of the user, stress and strain of parts of the user, angulation of particular parts of the user or sensors for monitoring physiological conditions such as the make up of the sweat or exudate of the user.

The temperature sensor may be any suitable thermocouple. Similarly, the biomechanical angulation sensor and the stress and strain sensors may be any suitable sensor including a conductive polymeric material or resistive change sensors that change in electrical resistance as a result of changes in angulation of parts of the body or forces such as the forces in posterior and anterior sections of a ankle or knee joint.

BRIEF DESCRIPTION OF THE DRAWINGS

An embodiment of the present invention will now be described with reference to the accompanying drawings, of which.

DESCRIPTION OF THE PREFERRED EMBODIMENT

An embodiment of the present invention will now be described in detail with reference to a sock shown in the Figures. However, it will be appreciated that the present invention may be embodied in any type of garment including, but by no means limited to stockings, leggings, underpants, long johns, singlets, inserts, inner socks, inner garments, under garments or bandages and may also be applicable in situations where the garment is used to cover the stump or terminated limb of the amputee that is fitted into a prosthetic limb.

The sock 10 according to the preferred embodiment has been specifically configured to be a comprehensive analytical and monitoring tool for patients having neuropathic or orthotic conditions. The sock has been devised with sensors that monitor biomedical movement and in particular measure force or pressure at desired positions on the load bearing surface, temperature of the patient's foot and optionally, stress or strain of the foot. Although it is beyond the scope of the present invention, the data obtained from the sensors can be analyzed by a qualified health care practitioner.

Figure 1:
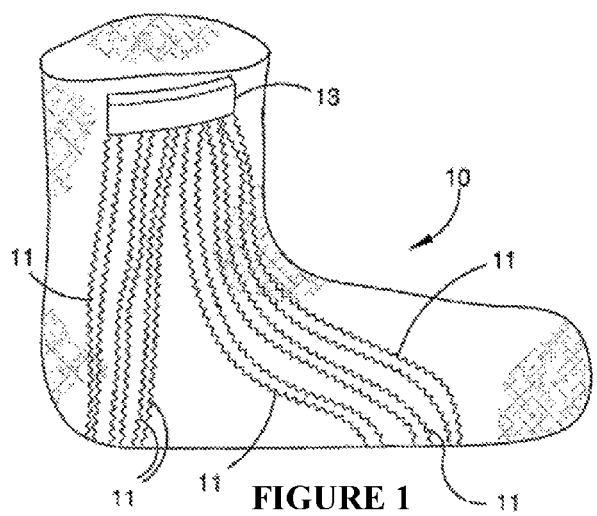
FIG. 1 is a perspective view of a sock having a detachable housing containing re-useable components of an electrical circuit that is fitted to the sock.
Figure 3:
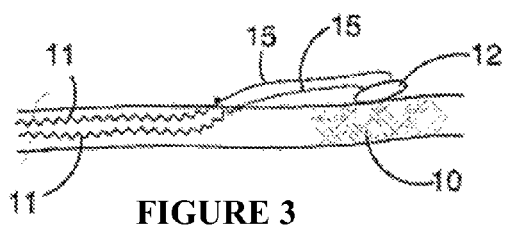
FIG. 3 is an enlarged cross-sectional view of one of the sensors of the sock shown in FIG. 1 or 2.

The sock shown in FIG. 1 comprises conductive yarns 11 such as silver coated yarns sewn to the outside face of the sock, sensors 12 located at the base of the sock 10 that may align with the heel and metatarsal regions of a foot wearing the sock 10, and a detachable housing 13 containing the electrical circuitry located on the upper end of the sock 10. Although it is possible that the yarns 11 may be elasticized which will allow the sock 10 to stretch and flex, in the situation where the yarns 11 are not elasticized, preferably the yarns 11 are sewn to the sock in a manner that allows stretching, for example, in a zig-zag or s-shaped pattern that allows the sock 10 to stretch and flex in the usual manner. The yarns 11 extend from the upper band of the sock 10 where the yarns 11 are arranged in pairs of terminating points 14 to the sensors 12 located on the base of the sock 10. As can be best be seen in the FIG. 3, the yarns 11 are sewn, knitted or otherwise incorporated into the sock 10 save for a length 15 of the yarn closest to the sensors 12 that is free from the base of the sock 10. In essence, the free length 15 of the conductive yarn allows the sensors 12 to be moved and positioned on the sock 10 at desired locations. The sensors 12 may be fixed in position using releasable adhesive, micro hook and loop type fasteners or an overlapping cover such as an adhesive tape that retains the sensors 12 in the desired position.

Figure 2:
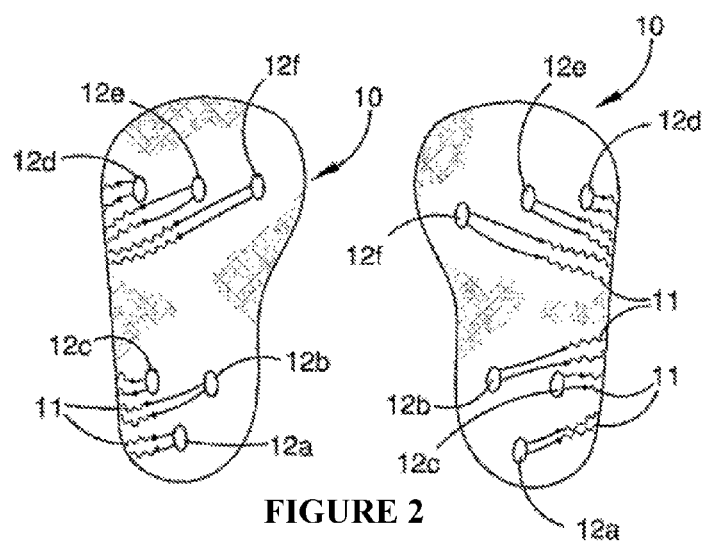
FIG. 2 is an underneath view of a pair socks that are substantially the same as the sock shown in FIG. 1, each sock having a set of sensors that are located on the sock so that, when the sock is worn, the sensors align with the metatarsal and heel of the foot.
Figure 16:
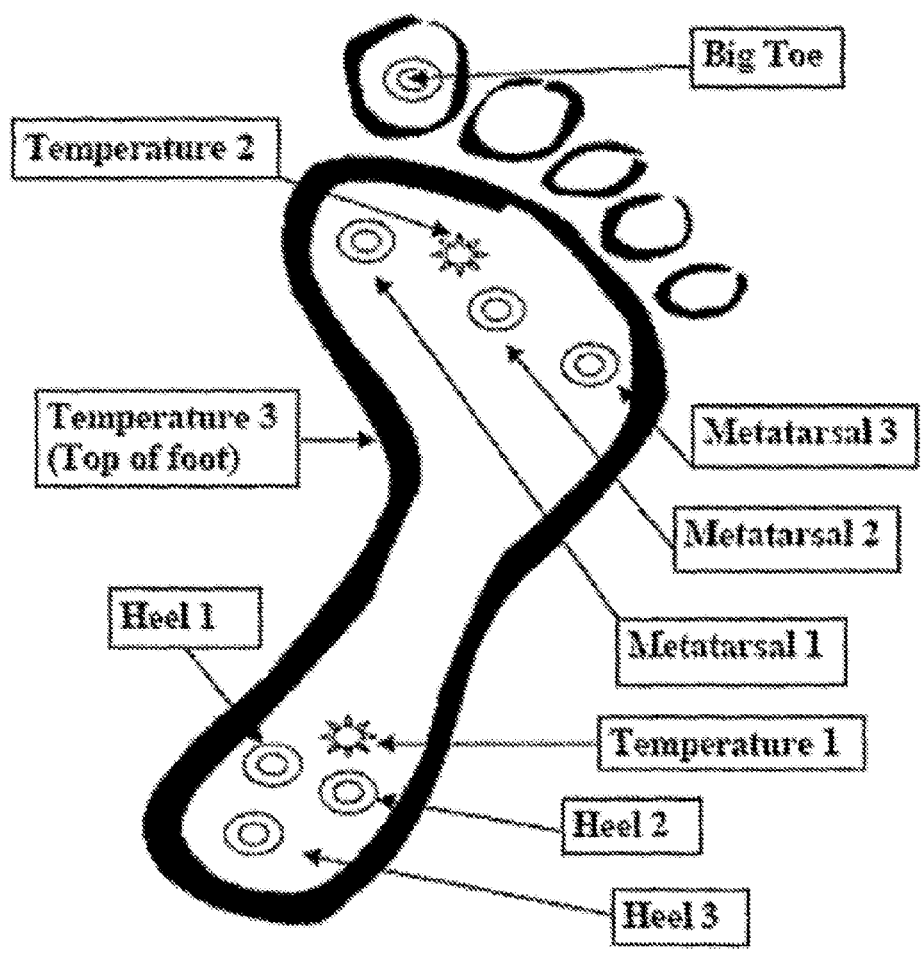
FIG. 16 schematically illustrates the sole of a foot and toes as if fitted with a series of pressure sensors.

As can be seen in FIGS. 2 and 16, preferably three pressure sensors 12a, 12b and 12c are located in the triangular formation at the heel of the sock 10 and, in addition, three separate sensors 12d, 12e and 12f are located on the sock 10 that align with the first, third and fifth metatarsal of a patient wearing the sock 10.

In our view an important characteristic of the sensors 12 that they have a low or thin profile, preferably in approximately 0.5 mm or less and have surface area in the range of 50 to 100 mm$^2$. One example of a pressure sensor 12 is a thin film sensors sold under the trade name FLEXIFORCE® by Tekscan, Inc. An advantage in the using a thin film sensor 12 is that the presence of the sensor 12 on the sock 10 does not cause an increase in pressure in the foot, stump or any other loading bearing surface that could cause an adverse physical effect to a medical condition such as neuropathy.

Although not shown in the Figures, temperature sensors or sensors for measuring any other physical or physiological condition may also be fitted to the sock. Examples of suitable temperature sensors are semiconductor type sensors or RTD type sensors or yarn and/or fabric type sensors.

Figure 4:
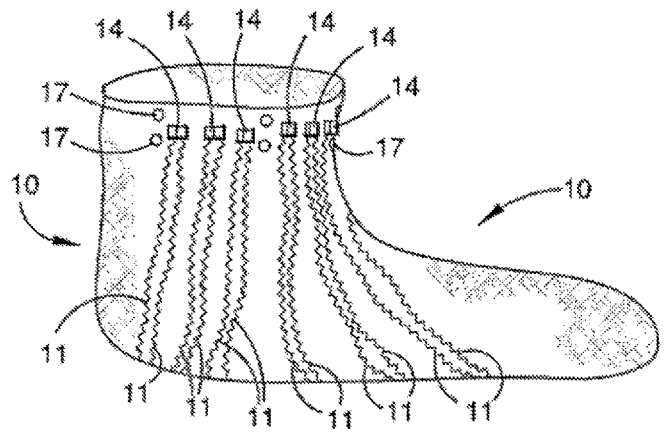
FIG. 4 is a perspective view of the sock shown FIG. 1 without the detachable housing fitted to the sock.
Figure 5:
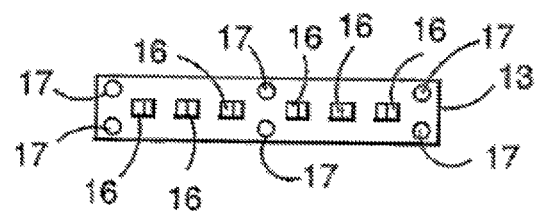
FIG. 5 is a back view of the detachable housing shown in FIG. 1.

The conductive yarns 11 extend from the sensors 12 at the base of the sock 10 to an upper edge of the sock 10 where the yarns end in pairs of terminating points 14. The terminating points 14 are arranged side-by-side and align with co-operating pairs of contact points 16 located on the underneath side of the detachable housing 13. Although not shown in the Figures, an electrical conductive adhesive sold under the trade name ARclad™ 8001 by Adhesive Research, Inc. Glen Rock Pa. 17327 is applied to either one or both of the terminating points or the contact points of the detachable housing 13. In addition to electrical coupling, the detachable housing 13 is also secured to the upper portion of the sock 10 using any conventional securing means such as buttons, straps and buckles, cooperating hook and loop type fasteners and, as illustrated in the FIGS. 4 and 5 press studs 17.

In order to allow the sock 10 to be worn by elderly, frail and patients with impaired or compromised bodily movement, preferably the detachable housing 13 is light weight and suitably less than 200 grams in weight. If necessary, the top band of the sock 10 can be reinforced with additional elastic to prevent movement of the sock 10 and housing during walking. Other means such as releasable adhesive or sticky adhesive may also be employed to ensure that the top band of the sock stays in a comfortable and working position. The detachable housing 13 contains electrical circuitry suitable for supply power to the sensors and receiving signals from the sensors. For example, the housing 13 contains a rechargeable battery, a processing unit that can be programmed with suitable algorithms able to be customized for particular applications, data storage and if desired, a transmitter that wirelessly sends signals to a host device or computer that the can further process data of the sensors worn by one patient or multiple patients wearing the sock simultaneously. The circuitry contained in the housing 13 may be made using any standard hardwiring.

Although it is ultimately dependent on the condition that is being monitored, in the situation where the sensors are monitoring pressure we have found that a primary data sampling rate of the sensors in the range of 500 to 1,500 Hz and suitably approximately 1,000 Hz to provide ample data. The optimal rate at which data from the sensors is sampled is dependant on a number of factors including:

the size of the power source available; and
the nature of the data required to provide meaningful feedback to the health care practitioner.

In addition, the processing unit may carry out data modification or manipulation, for example, noise reduction, to moderate the amount of the data required to be stored. In any event, ideally the available data memory and power supply are capable of the continuous operation for a period of at least one day. The status of the patient's condition can change over the course of a day and, therefore, the device should be able to operate for a period of at least one day.

The sock will have immediate application in the podiatry and orthopedic fields to provide extensive data regarding walking behavior with and without footwear and on all surfaces. The sock may also be applied to specialized limb socks in the prosthetic field. This data could be used to diagnose the onset of problems related to particular parts of the foot or limb.

In neuropathic conditions, where there is a decline in the efficiency of the venous system due to disease, the indication from temperature and pressure sensors may be effective in diagnosing problems. A change in walking behavior, as a person becomes less conscious about foot movement, due to fatigue, or a decline in nervous response as a consequence of their neuropathy, or certain risk walking patterns, is either not detectable or not easily detectable by present devices. There also may be footwear related issues that are not apparent from current measuring systems.

Long term, time based, measuring of actual pressure at key indicating points of a foot combined with temperature measurements and other measurements like strain could provide a strong indication of a degenerating condition that could result in a pressure ulcer. In addition to the diagnostic function of the sock there is provided a monitoring function via a means to wirelessly transmit the data to local or remote systems. This could provide warnings to the wearer or to care providers about at risk conditions.

Figure 6:
FIG. 6 is a photograph of a sock substantially the same as that shown in FIGS. 1 to 5.
Figure 7:
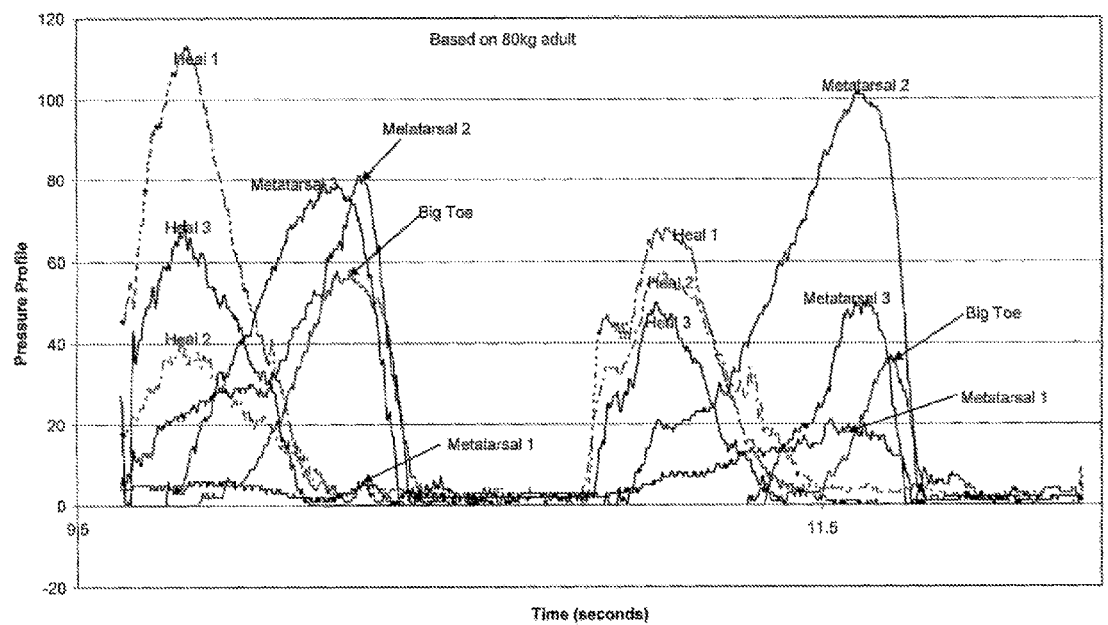
FIG. 7 is a graph illustrating a set of results obtained using the sock shown in FIG. 6.

FIG. 7 is a graph illustrating a set of data obtained using the sock shown in FIG. 6. The graph illustrates data obtained from pressures sensors located at the heel, fifth metatarsal, third metatarsal, first metatarsal and big toe. The date shown in the graph was obtained by the patient walking from a hard concrete floor to a soft carpeted surface. The different sensor responses provide a clear indication of the walking behavior and characteristics.

In addition, the sock could also provide a means to analyze athletic behavior for running, walking and jumping in time based pressure, temperature and strain measurements. For example running patterns under stress may provide an insight into endurance levels, the onset of physical problems or a means to correct or improve running action. This type of analysis may assist in developing corrective solutions. The data may also provide an analysis of the physical capability of athletes as it could indicate a change in running or walking patterns as the limits of endurance are reached. This could provide valuable information for coaches.

In another example, rather than using the thin film sensor described above it is possible for the 35 sensor to be a substrate having surfaces that are treated with a conductive polymer such as polypyrrole or poly(ethylenedioxythiophene) (PEDOT) and has variable conduction or resistance depending on the force applied to the substrate.

Those skilled in the art will appreciate that many modifications and variations may be made to the preferred embodiment described above without departing from the spirit and scope of the present invention.

The sock 10 may be any conventional sock 10 that has been retro-fitted with the required elements according to the present invention or alternatively a specialized sock that has been purposely built. Moreover, the sensors may be fitted or removably connected to a substrate in any form including bandages, inserts that are worn under or over a conventional item of clothing such as socks, stockings, underpants and alike. For example, in the situation where the sensors are monitoring pressure on a wearer's feet, the substrate may be in the form of a mini sock or ankle sock that only comes up to the ankle of the wearer and a conventional sock is then fitted over the mini or ankle sock.

According to another embodiment, any one or a number of sensors for monitoring physical conditions such as temperature, stress, strain or angulation and/or sensors for monitoring physiological conditions such as the make up or properties of sweat and body exudate may be included.

According to yet another embodiment, it is possible that the part of the electronic circuitry contained in the housing 13 may be in the form of printed electronic circuitry. The printed circuitry may be contained wholly or partly within the housing or partly or wholly on the substrate.

Further Examples

As described above, the present invention may be embodied in any type of garment including, but by no means limited to stockings, leggings, underpants, long johns, singlets, inserts, inner socks, inner garments, under garments or bandages and may also be applicable in situations where the garment is used to cover the stump or terminated limb of the amputee that is fitted into a prosthetic limb. In addition to the analysis of foot or limb related activity, the garment may also be used in a broad range of analysis or monitoring of medical conditions.

An effective and widely used means for treating venous leg ulcers and various wounds is application of pressure bandages. As an example leg ulcers are a chronic condition caused by a range of clinical disorders, either individually or in combination but to a large extent are associated with underlying venous/arterial disease. The incidence of ulceration in the population increases with ageing. Diabetes is a condition that is a significant cause of ulceration.

Another condition where use of pressure garments or bandages are useful is Lymphoedema, a chronic swelling of the limbs due either to a poor lymphatic system that fails to adequately drain fluids or can be the result of surgery or radiotherapy. There is a high potential for development of leg ulcers known as lymphatic obstruction oedema.

The use of compression bandages is now generally accepted as an effective means to minimize or reverse the negative vascular changes by forcing fluid from the interstitial spaces back into the vascular and lymphatic systems. Generally though, the correctly applied pressure will be reduced progressively up the limb or leg and it is usual that external compression bandages are applied in a graduated fashion, with the highest pressure at the ankle.

However the actual pressure required remains a matter of some debate as there is not currently a means to effectively measure and monitor the pressure at the skin once bandages have been applied and patients leave a clinician. Pressures ranging from 15 to 50 mm of Hg have been described although there is debate on what is appropriate for various patients an~their conditions. Pressures of about 40 mmHg at the ankle are widely quoted in the literature for the prevention or treatment of venous leg ulcers, but some authorities recommend values significantly higher than this.

The pressure exerted by any pressure bandage is determined by the elasticity of the fabric, the physical shape of the limb, the number of fabric layers applied to the limb and the manner of application. There are many bandage systems, comprising 1 or more layers, available for providing a pressure gradient. A bandage correctly applied with constant tension to a limb of normal proportions will automatically produce graduated compression with the highest pressure at the ankle. This pressure will gradually reduce up the leg as the circumference increases. However there is no uniformity in limb shapes and dimensions so that there are great variations for patients that can only be controlled by the expert experience of the clinician applying the bandages. Too little pressure or an inadequate gradient will be ineffective in the healing process, too high a pressure can result in localized pressure points that could lead to complications.

There is little actual pressure data to determine the effects of pressure on the wide population affected by such conditions and even less data available on the effect when an individual moves from a supine to a standing position or sits for extended time. For example if blood collects in the vessels and sinuses of the lower leg, under the influence of gravity, causes the volume of the leg to increase and is associated with the formation of oedema, leg volume will increase and lead to pressure changes.

It is dependent on clinicians who are expert in the choice of products for particular patients and the optimum means for applying any particular product to avoid these complications.

The present invention may be used in a broad range of applications including bandages or pressure bandages in the sense described above. One of the advantages provided by this particular embodiment of the present invention is that effective measurement of the pressures applied by pressure bandages and a valuable means to determine the pressure gradient created by any pressure bandaging system. In addition it can also provide a means to determine the performance of pressure bandaging on patients while the bandages are in use and the effect on the patient when moving from supine to standing positions.

According to another embodiment of the present invention, the garment may be in the form of a high stretch low pressure producing fabric sleeve that can be readily applied to a patient. The sleeve has a number of pressure and temperature sensors and conducting circuits from each sensor to a common termination point at one end of the sleeve. As with the sock the sensors/sleeve is able to be readily connected, or disconnected from, to a removable electronics band or small device that provides power for the sensors and is able to then transmit the sensor data to a remote device for data analysis or simple display. In another form the pressure and temperature sensors are contained in a wrap around fabric to be used as a first layer prior to application of the pressure producing bandages.

Once in place on a patient's limb preferred pressure bandages are applied in a manner to produce the desired pressure gradient that is readily displayed as the bandages are applied.

It should be appreciated that this approach is not limited to fabrics or sleeves directed at limbs but can be applied to other garments. For example the sensors could be incorporated into undergarments for use by paraplegics or quadriplegics to sense the contact with seat or other surfaces to determine and alert whether there are risks for developing pressure points that could lead to complications.

The pressure sensors used in the present invention may be in a number of different forms. For example, pressure sensors from Tekscan are one form of sensor that can be used. An alternative sensor is the type of sensor in which a substrate, such as a substrate made from wool fibre, is treated with conductive polymers such as polypyrrole or poly(ethylenedioxythiophene) (PEDOT).

Techniques for applying conductive polymers to flexible substrates include, but are by no means limited to the following known techniques: roll to roll coating, inkjet printing dispersions and physical vapor deposition. Furthermore, examples of two journal articles that describe techniques for applying conductive poly.mers to a base fabric substrate suitable for use as a pressure sensor are as follows.

1. ADVANCES AND APPLICATIONS OF INHERENTLY CONDUCTIVE POLYMER TECHNOLOGIES BASED ON POLY (3,4-ETHYLENEDIOXYTHIOPHENE) by Simpson et al, 2005 AIMCAL Fall Technical Conference and 19fu International Vacuum Web Coating Conference, Oct. 16-20, 2005

2. APPLICATION OF POLYPYRROLE TO FLEXIBLE SUBSTRATES by Winter-Jensen, Clark et al.

The performance of fabric samples treated with a polypyrrole and PEDOT will now be described in further detail.

Figure 8:
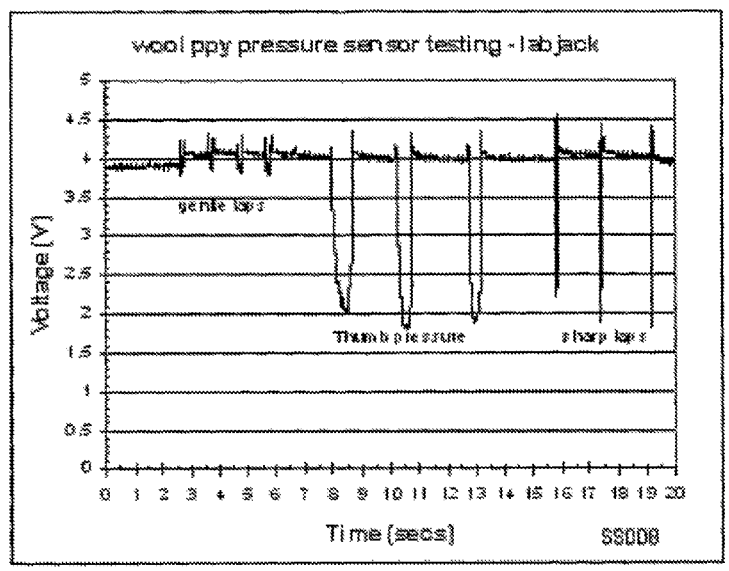
FIG. 8 is a graph illustrating the changes in voltage measured across a wool polypyrrole pressure sensor.

FIG. 8 illustrates the test results of a wool fabric sensor treated with a polypyrrole conductive polymer. The test was carried out using a Labjack data collector to detect relative responses between gentle taps, thumb pressure and sharp taps applied to the fabric. As can be seen, the conductivity of the material increases and thus the potential difference reduces with pressure applied to the fabric.

The pressure sensing performance of a fabric treated with a conductive poly.mer is to an extent dependent on the compressibility performance of a fabric. The compression of fabric can be measure in two forms, namely a static test in which a weight is placed 30 on the fabric and a dynamic test whereby a weight is dropped onto the fabric.

Figure 9:
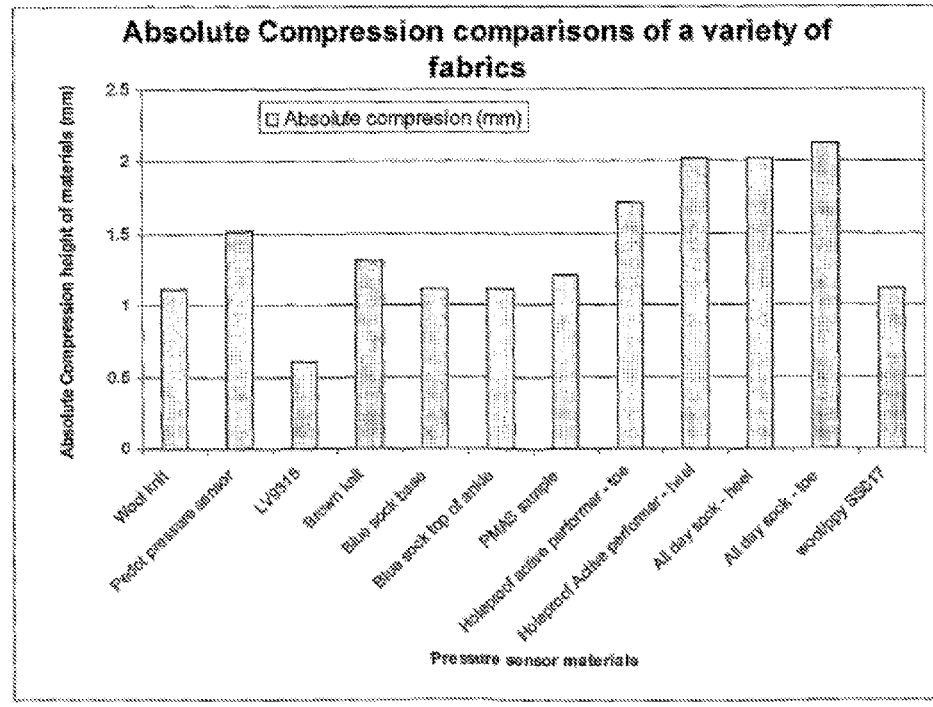
FIG. 9 is a chart showing the compression properties of a range of fabrics measured using a Hounsfield Jaw.

A variety of fabric types were trialed to determine the relative compression characteristics, with the thought that the more compressible fabrics would have a better range as conductive pressure sensors. A Hounsfield test equipment apparatus H5000M was used to exert a controlled pressure (maximum applied weight=50 Kg or 530 N) onto the chosen fabric pieces and the compression noted. A calibration graph was first prepared for jaw separation distance, to enable the relative fabric compressions to be calculated from the resultant mV readings obtained at maximum possible compressions. Once the device was calibrated the compression characteristics for a set of different fabrics was measured. The compression characteristics of a set of fabrics tested is set out in FIG. 9. Fabrics having poor total compression were determined to be unsuitable for treatment with a conductive polymer. Absolute compression heights of at least 1.0 mm where determined to be the most suitable.

Figure 15:
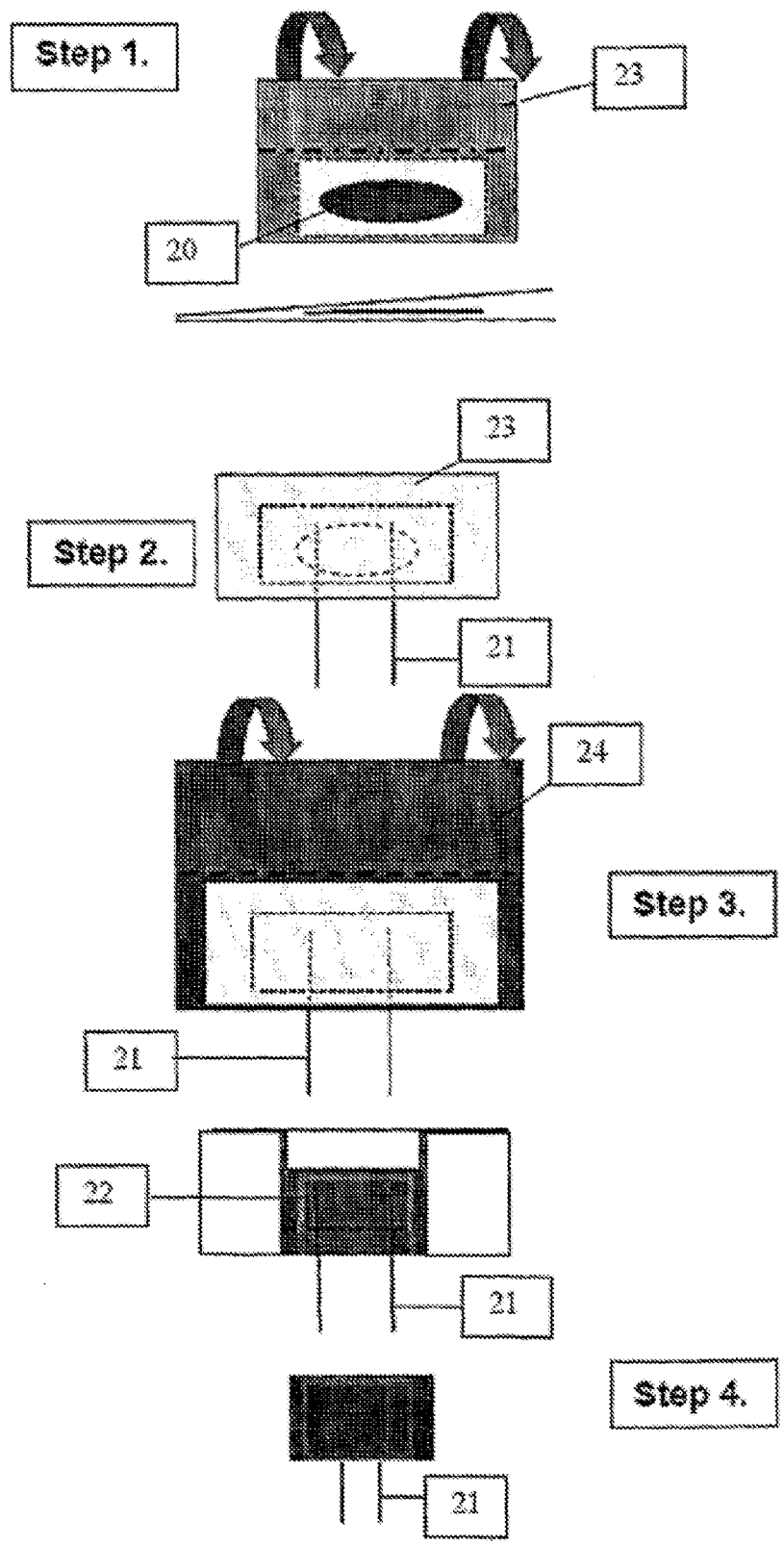
FIG. 15 schematically illustrates a series of steps for manufacturing a fabric sensor treated with PEDOT.

A PEDOT wool sensor was constructed in accordance with the sequence of steps set out in FIG. 15 and then tested. The step 1 involves applying a conductive poly.mer a section of sock fabric identified by reference numeral 20 in accordance with techniques such as those discussed in the above journal articles. Conductive threads in the form of silver coated threads 21 are spaced approximately 5 mm apart are then sewn into the conductive poly.mer section and non-conductive thread 22 is sewn around the outside of the conductive material. A lightweight greaseproof paper 23 is then folded over the sensor to form a paper envelope over the sensor. A waterproof medical gown fabric 24 is then wrapped around the sensor. Finally excess material is cut away from the sensor.

Figure 10:
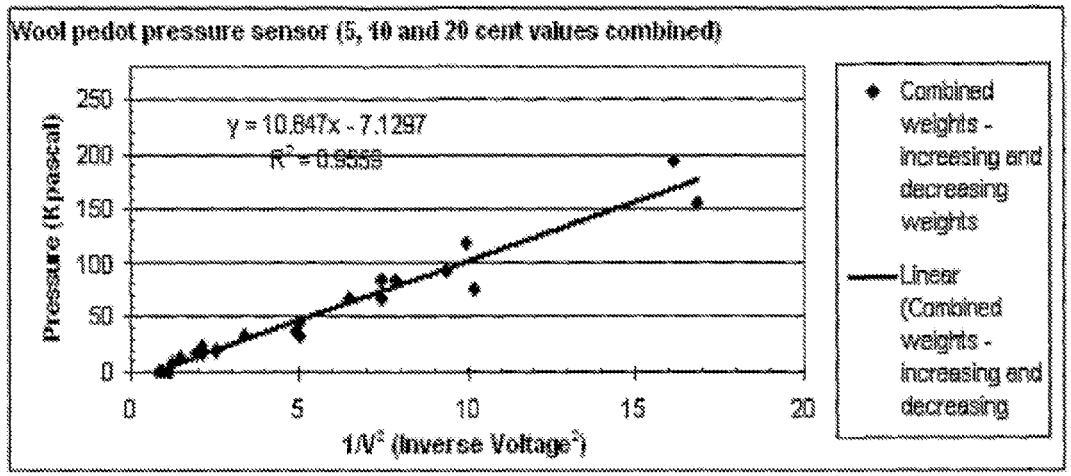
FIG. 10 is a graph illustrating the relationship between the pressure measurements and an inverse of voltage squared of a fabric sample treated with PEDOT.

Static tests were then conducted on the sensor shown in FIG. 15 over a range of different pressures using a Hounsfield Jaw apparatus. The results obtained show a relationship between the pressure applied and $1/V^2$ which is illustrated by the graph in FIG. 10.

Figure 11:
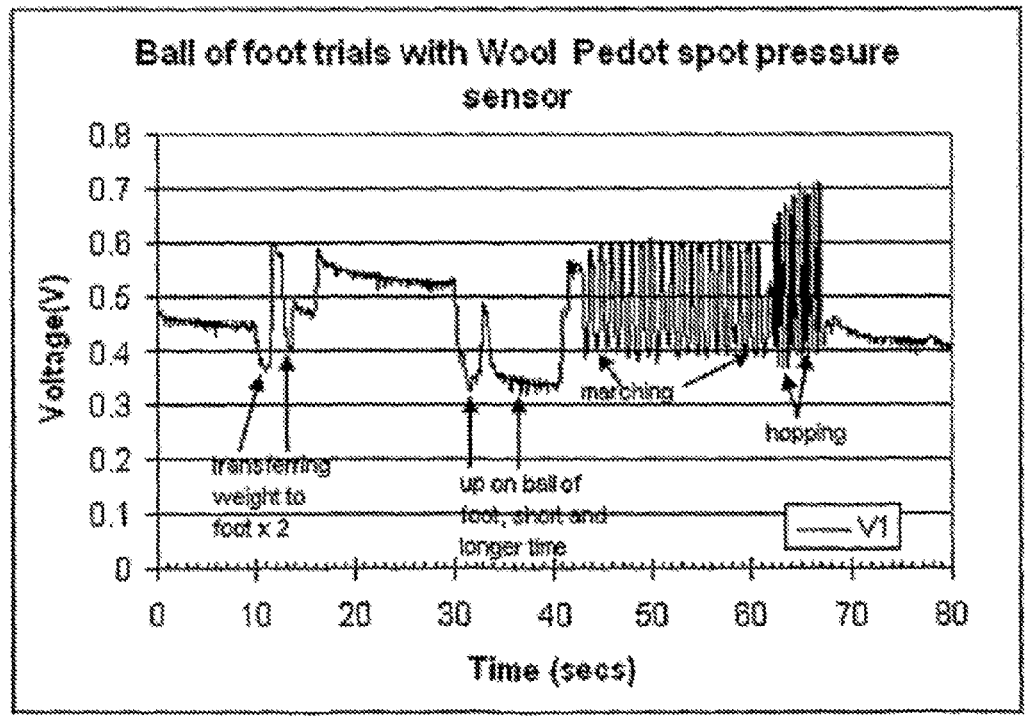
FIG. 11 is a graph illustrating changes in voltage across a sensor in the form of a wool fabric treated with PEDOT located on the ball of a foot of a wearer during a trial.
Figure 12:
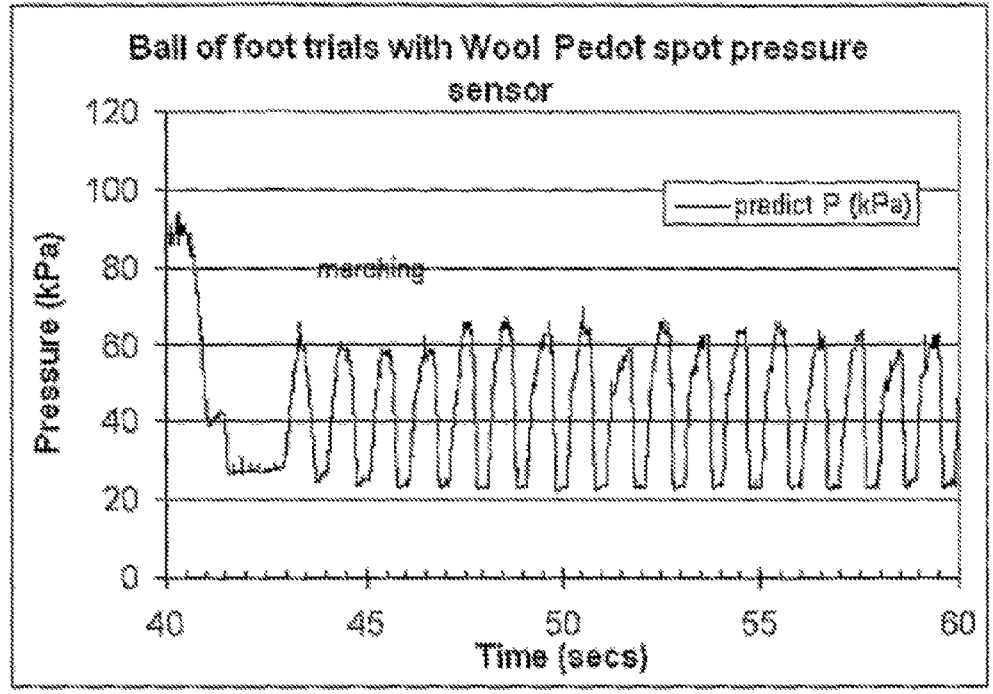
FIG. 12 is a graph illustrating an enlarged view of the graph of FIG. 11 over the time interval between 45 and 60 seconds.

Two identical sensors constructed in accordance with FIG. 16 were then located in the ball and heel of a wearer in the weight range of 65 to 70 kg and then asked to perform a series of separate movements. FIG. 11 illustrates the results obtained of a sensor located at the ball of the wearer's foot when requested to carry out activities. Specifically, the initial dips between 10 and 15 seconds indicate the wearer transferring all of their weight between standing on two feet and standing on one foot fitted with the sensor. The interval between 30 and 40 seconds represent a wearer taking the weight off their heels and the interval from 40 to 60 seconds represents a wearer marching while the interval from 63 second to 70 seconds presents the wear hopping. FIG. 12 is an enlarged view of FIG. 11 over the interval 45 to 60 seconds.

Figure 13:
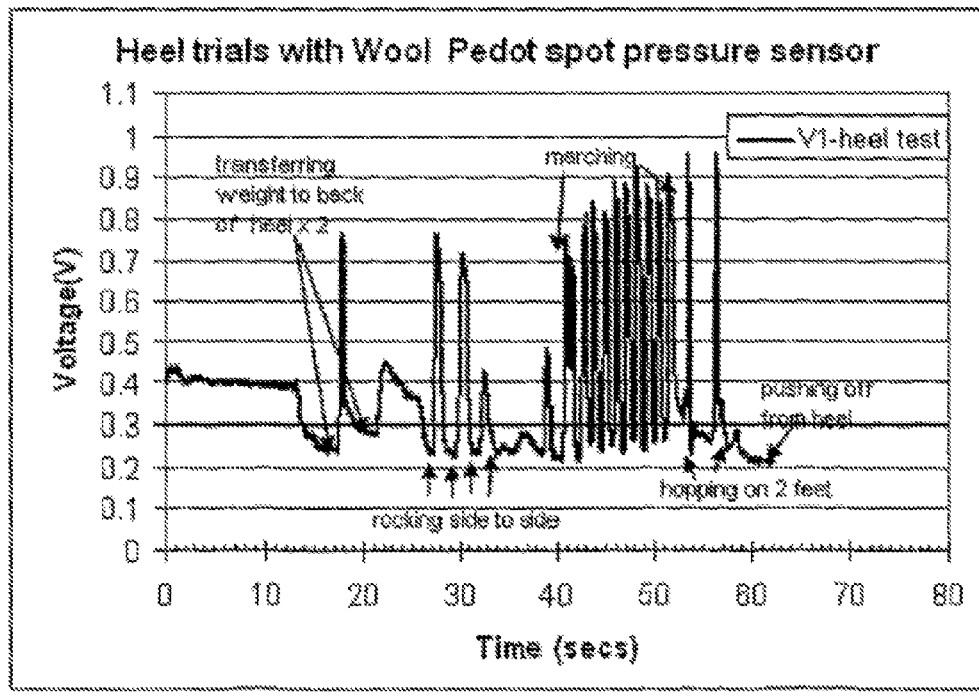
FIG. 13 is a graph illustrating changes in voltage across a sensor in the form of wool fabric treated with PEDOT located on the heel of a foot of wearer during a trial.

FIG. 13 illustrates the response obtained from a sensor located at the heel of the wearer while the wearer perfor.ms a series of different movements. In particular, during the interval 15 to 25 seconds, the wearer transfers their weight from a position in which their weight is evenly distributed on their feet to a position in which their weight is unevenly distributed to the heel followed by a rocking motion forward and then finally back again onto the back of the heel. The interval from 28 to 35 seconds represents the wearer rocking from side to side. The interval from 40 to 50 seconds represents the response from the marching and 30 the interval from 55 to 60 seconds represents the response obtained during hopping on two feet.

Figure 14:
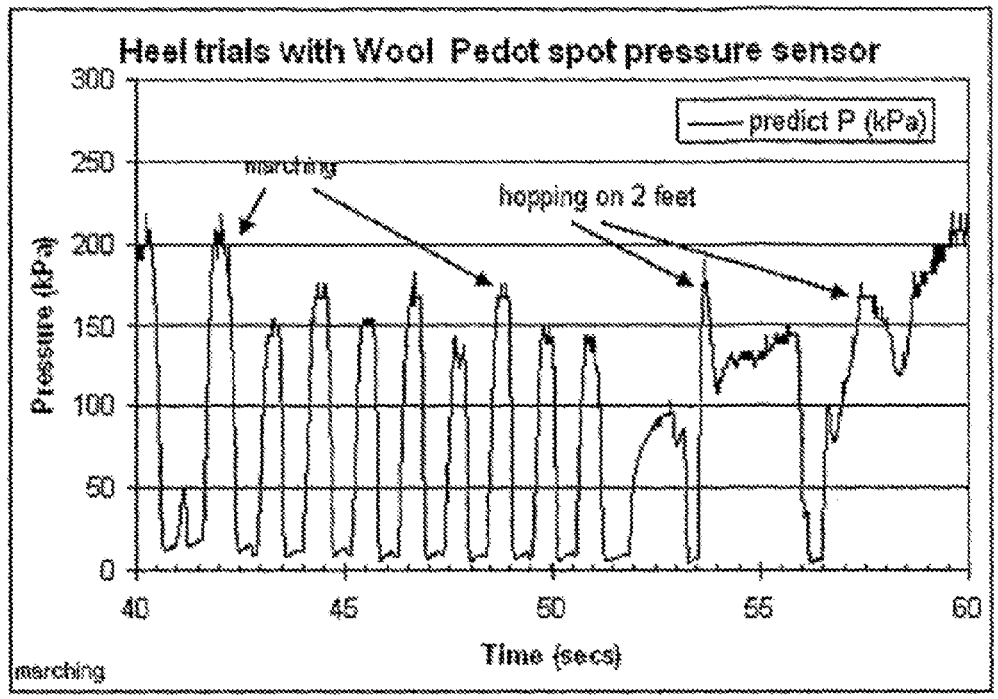
FIG. 14 is a graph illustrating an enlarged view of the graph of FIG. 13 over the time interval between 40 and 60 second.

FIG. 14 is an enlarge view of the response during marching and hopping activities during the interval from 40 to 55 seconds.

A trial was then run in which both PEDOT fabric sensors and Tekscan Flexiforce sensors were operated simultaneously. The trial involved 3 single PEDOT jersey sensors placed on the inner and outside heel positions, namely positions H1 and H2 in FIG. 16 and a double interlock knit PEDOT sensor placed in the middle heel position H3. Tekscan sensors were placed on the remaining foot pad and big toe position, identified in FIG. 16 as M1, M2, M3 and BT. The trial was carried out by the sock being worn around the laboratory, for a period of 1.5 hours.

Figure 17:
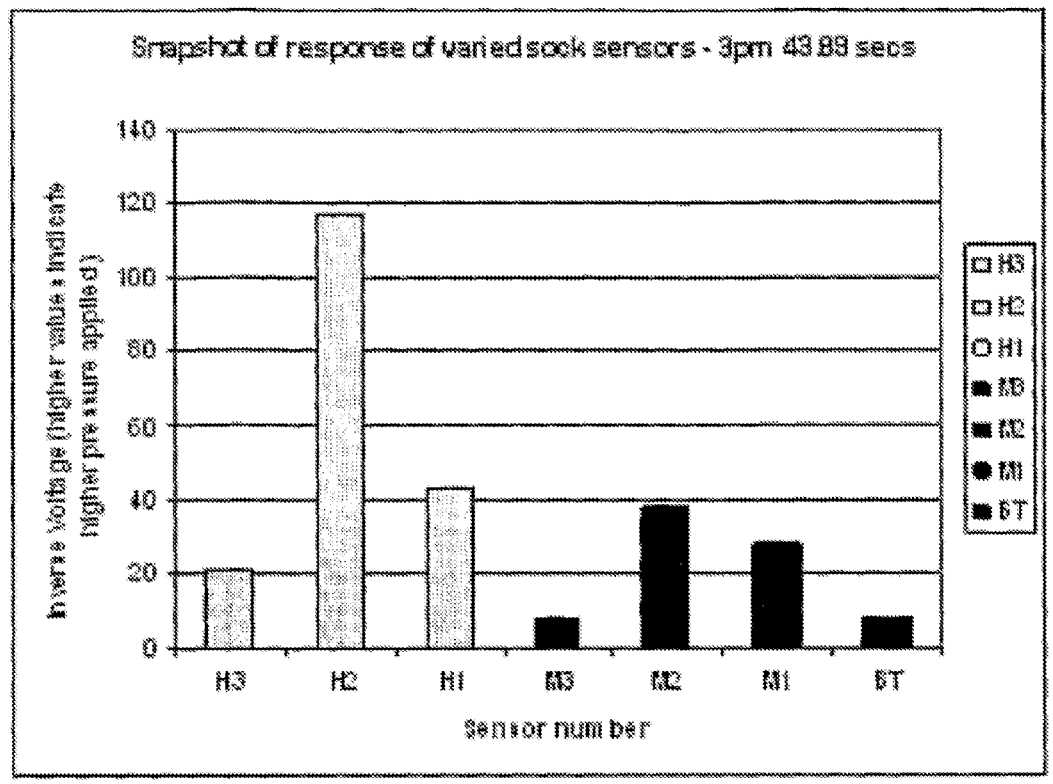
FIG. 17 is a bar graph illustrating a set of signals of the sensors shown in FIG. 16 during a trial.

FIG. 17 is a graph showing an instantaneous output for the sensors in order of Left to Right: H3, 15 H2, H1, M3, M2, M1 and BT.

At the end of the trial all sensors were tested using the Hounsfield Jaw apparatus and all were measured as having pressure responses as a function which caused an inverse voltage change. Thus, all sensors were shown to be responsive and still in working order after the trial.

We claim:

1. A system that is wearable by a person to monitor or sense pressure, the system including:
    a) a flexible substrate in the form of a garment that can be worn by or fitted directly or indirectly to surfaces of the person; and
    b) at least one pressure sensor integrally incorporated into the substrate, with leads extending from each pressure sensor, the leads terminating in contact surfaces located on an external surface of the flexible substrate and spaced a distance from an edge boundary of the flexible substrate.

2. The system according to claim 1, wherein the at least one pressure sensor comprises a material selected from the group consisting of: conductive yarns or threads and metal coated threads or yarns.

3. The system according to claim 1, wherein the at least one pressure sensor comprises substantially inert electrodes to measure a change in electrical potential difference across the sensor.

4. The system according to claim 1, wherein the at least one pressure sensor comprises a material selected from the group consisting of: conductive yarns or threads and conductive polymers that are spaced apart by a spacing in the range of 2 to 15 mm in a direction transverse to the direction in which the substrate compresses.

5. The system according to claim 1, wherein the at least one pressure sensor has an area substantially transverse to a direction of pressure application that is equal to or less than 400 mm$^2$.

6. The system according to claim 1, wherein the at least one pressure sensor is used for monitoring biomechanical movement of the person's foot and is located at a toe, heel, metatarsal or arch region of the person's foot.

7. The system according to claim 1, wherein at least one pressure sensor is located at a part of the body required to carry the load of the person while walking or sitting.

8. The system according to claim 1, wherein at least one pressure sensor is located at a sole of the person's foot while walking.

9. The system according to claim 1, wherein at least one pressure sensor is located at a buttock of the person while seated.

10. The system according to claim 1, wherein at least one pressure sensor is located at a part of the body not required to carry the load of the person while walking or sitting.

11. The system according to claim 1, where at least one pressure sensor is located at a side surface of the ankle or an upper part of the foot.

12. The system according to claim 1, wherein the substrate is a garment in the form of one of socks, stockings, underpants, long johns, a singlet, leggings, inserts, inner socks, inner garments, under garments, bandages, pads, inserts, tubular sleeves, or garments used to cover a stump or terminated limb.

13. The system according to claim 1, wherein the at least one pressure sensor can be used to monitor the level of pressure applied to the person by an external source, and the flexible substrate is in the form of a compression garment.

14. The system according to claim 1, wherein the substrate comprises a woven fabric, a non-woven fabric, or a knitted fabric.

15. The system according to claim 1, wherein the flexible substrate and the at least one pressure sensor can be worn directly against surfaces of the person.

16. The system according to claim 1, wherein the flexible substrate and the at least one pressure sensor can be worn indirectly against surfaces of the person.

17. The system according to claim 1, wherein the substrate is in the form of a sock and the leads terminate in contact surfaces located at an ankle region of the sock.

18. The system according to claim 1, additionally comprising electrical circuitry that receives signals from the contact surfaces located on the substrate that communicates with the at least one pressure sensor, wherein the electrical circuitry is provided in a first housing that is connectable to and disconnectable from the contact surfaces located on the substrate as desired.

19. The system according to claim 18, wherein the circuitry provided in the first housing includes reusable components of an electrical circuit including: signal conditioning components; data storage; data processing units; and data transmission units.

20. The system according to claim 1, additionally comprising electrical circuitry that receives signals from the contact surfaces, wherein the electrical circuitry is provided in a first housing that is connectable to and disconnectable from the contact surfaces located at the ankle region of the sock.

21. The system according to claim 1, wherein the leads comprise conductive fibers, yarns, threads, coated threads or coated electrical ribbon that are sewn, knitted or woven into the substrate.

22. The system according to claim 1, wherein the leads are supported on the substrate so as to move between a corrugated or tortuous condition when the substrate is not flexed or stretched and an at least partially straightened condition when the substrate is flexed or stretched.

23. The system according to claim 1, additionally comprising at least one additional sensor capable of monitoring at least one of: temperature, stress, strain, angulation, sweat composition, and a physiological condition of the person.

24. The system according to claim 1, wherein the at least one pressure sensor comprises a surface treated with a material having a variable resistance depending on the force applied to the substrate.

25. The system according to claim 24, wherein the material is a polymeric material comprising polypyrrole or poly(ethylenedioxythiophene).

26. The system according to claim 1, wherein the at least one pressure sensor comprises a thin film sensor.

27. A garment that is wearable by a user to monitor or sense pressure either separately or in combination with any one or more of temperature, stress, strain, angulation, sweat composition or a physiological condition, the system including:
    a) a flexible substrate that can be worn by, or fitted directly or indirectly to surfaces of a user subject to pressure or forces; and
    b) at least one discrete pressure sensor that is integrally incorporated into the substrate having conductive leads that are sewn, knitted or woven to the substrate and terminate in contact surfaces located on an external surface of the substrate and spaced a distance from an edge boundary of the substrate, wherein the substrate and sensors can be worn directly or indirectly against surfaces of the user and the sensors can be positioned at desired locations without causing an increase in pressure on load bearing surfaces as result of the presence of the pressure sensors.

28. A method of monitoring a subject, the method including the steps of:
    placing a garment comprising a flexible substrate having one or more discrete pressure sensor(s) with conductive leads terminating in contact surfaces located on an external surface of the flexible substrate and spaced a distance from an edge boundary of the flexible substrate in contact with a buttock, hand, foot or limb of the subject;
    mounting circuitry containing cooperating contacts that electrically connect to the contact surfaces located on the garment to position the circuitry on the garment substrate; and
    monitoring pressure readings attributable to either the weight of the patient or the pressure applied externally to the subject.

29. The method according to claim 28, comprising placing a pressure sensitive garment in contact with the foot of the subject, wherein the at least one discrete pressure sensor is located on a part of the subject's foot including a ball, heel, toe, side ankle surface or upper part of the subject's foot.

30. The method according to claim 28, additionally comprising positioning contact surfaces of a detachable housing in contact with the contact surfaces located on the external surface of the garment, wherein the detachable housing additionally comprises data storage and data transmission capability.

* * * * *